United States Patent [19]

Smart et al.

[11] Patent Number: 5,557,018
[45] Date of Patent: Sep. 17, 1996

[54] PARTIALLY FLOURINATED POLYMERS AND PROCESS THEREFOR

[75] Inventors: Bruce E. Smart; Zhen-Yu Yang, both of Wilmington, Del.

[73] Assignee: E. I. du Pont de Nemours and Company, Wilmington, Del.

[21] Appl. No.: 527,799

[22] Filed: Sep. 13, 1995

Related U.S. Application Data

[62] Division of Ser. No. 312,722, Sep. 27, 1994, Pat. No. 5,475,071.

[51] Int. Cl.$^6$ .................................................. C07C 21/18
[52] U.S. Cl. .............................................. 570/135; 570/134
[58] Field of Search ...................................... 570/134, 135

[56] References Cited

U.S. PATENT DOCUMENTS

| | | | |
|---|---|---|---|
| 4,897,457 | 1/1990 | Nakamura et al. | 526/247 |
| 4,997,855 | 3/1991 | Peake | 570/135 |
| 5,015,790 | 5/1991 | Hung | 570/126 |
| 5,260,492 | 11/1993 | Feiring | 568/685 |
| 5,313,003 | 5/1994 | Kruger et al. | 568/669 |
| 5,326,917 | 7/1994 | Feiring et al. | 526/247 |
| 5,336,741 | 8/1994 | Yang | 526/247 |

OTHER PUBLICATIONS

"The Preperation and Allylation of Perfluoroally Cadmium and Copper Reagants"by Burton et al. J. of Fluorine Chemistry, 50 (1990), pp. 257–263.
"1, 6–Heptadiene" Aldrich Chemical Catalog, p. 784 1988–1989.
Fearn, J. E. et al, *J. Polym. Sci., A–1, 4, 131–140, (1966)*.
Brown, D. W. et al, *J. Polym. Sci., A–2, 7, 601–608, (1969)*.
Burton, D. J. et al, *J. Fluorine Chem., 50, 257–264, (1990)*.

*Primary Examiner*—Tae Yoon

[57] ABSTRACT

Selected partially fluorinated $\alpha,\omega$-dienes can be (co)polymerized to form polymers in which cyclic structures are present. A novel free radical polymerization process, in which the polymer obtained is dependent on the initiator used, is described. The polymers are useful for films, coatings and molded parts.

1 Claim, 2 Drawing Sheets

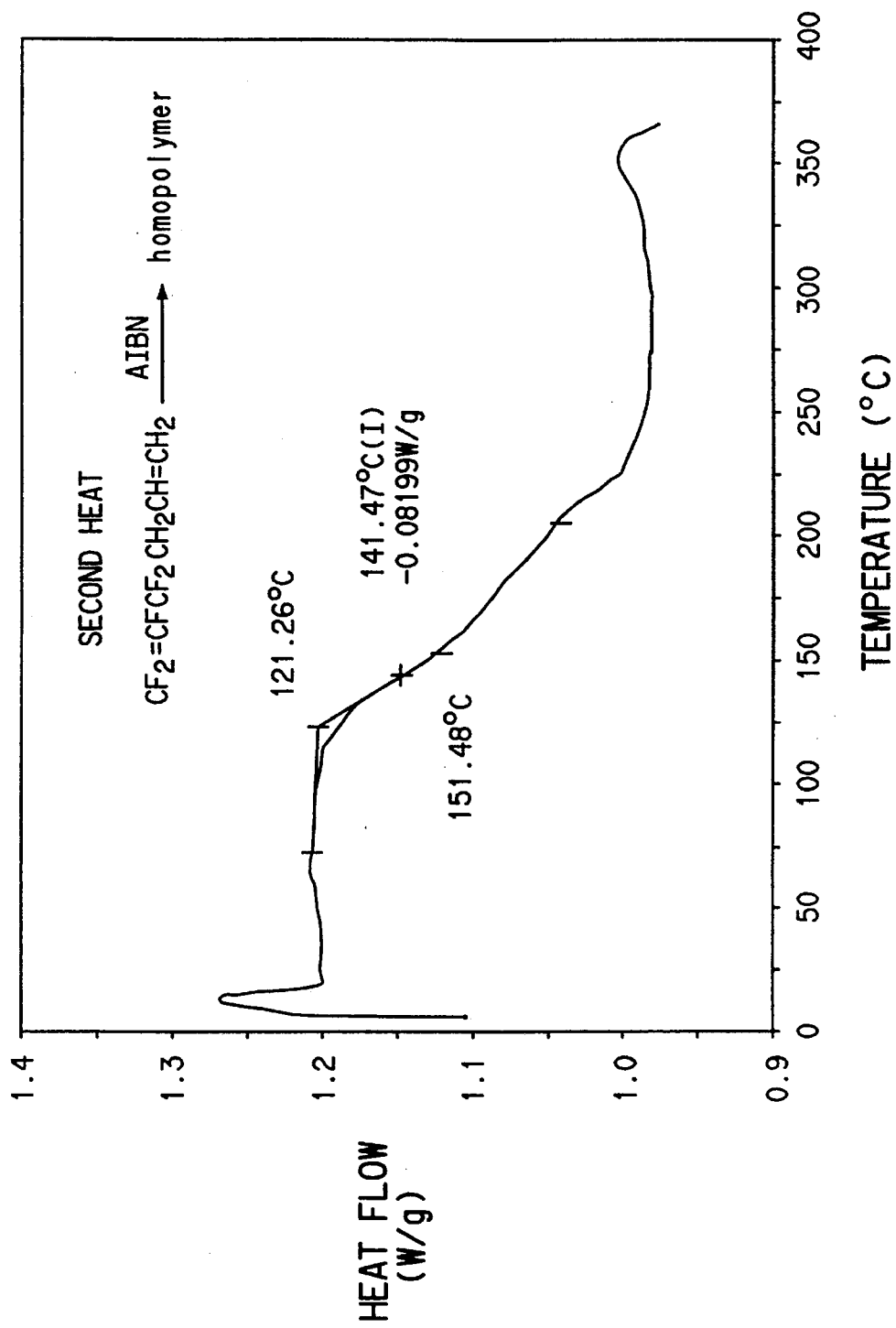

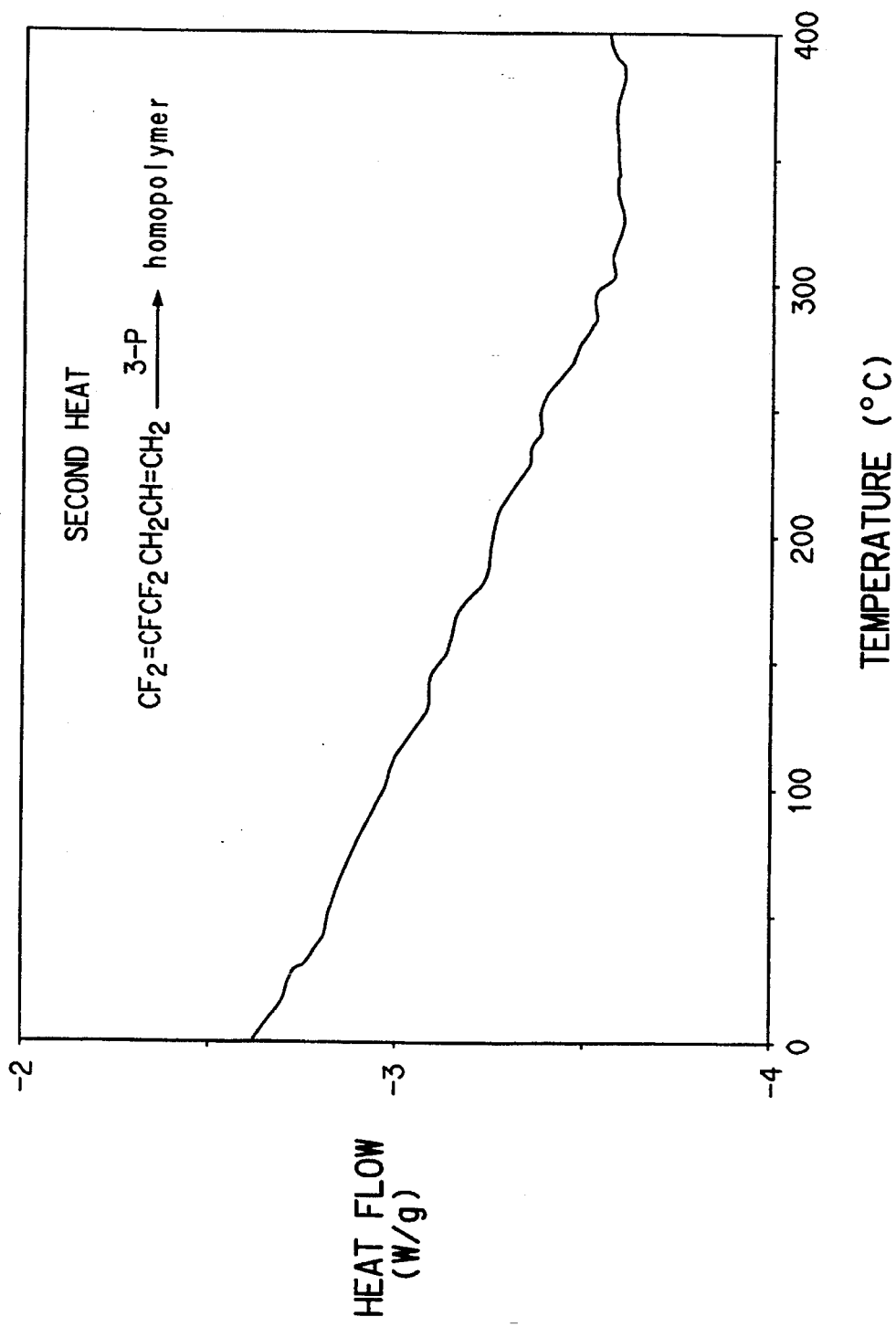

PARTIALLY FLOURINATED POLYMERS AND PROCESS THEREFOR

This is a divisional of Ser. No. 08/312,722, filed Sep. 27, 1994, now U.S. Pat. No. 5,475,071.

FIELD OF THE INVENTION

This invention concerns polymers made from selected partially fluorinated dienes, in which the repeat units are cycloaliphatic. Also disclosed is a novel monomer, and a free radical polymerization process for making such polymers.

TECHNICAL BACKGROUND

Free radical polymerizations which include nonconjugated dienes (and bis vinyl ethers) usually yield polymers which are crosslinked because of the "separate" reaction of each of the double bonds with the free radicals in the reactions. However, it is known that in some instances perfluorinated or partially fluorinated compounds containing two such double bonds do not form crosslinked polymers, but form polymers containing cyclic structures.

U.S. Pat. Nos. 5,326,917, 5,313,003, 5,260,492, 4,897, 457, J. E. Fearn, et al., J. Polym. Sci. A-1, vol. 4, p. 131–140 (1966) and D. W. Brown, et al., J. Polym. Sci. A-2, vol. 7, p. 601–608 (1969) all describe the polymerization of partially or fully fluorinated compounds containing two double bonds which give polymers having cyclic structures. The instant monomers and polymers are not disclosed therein.

Commonly assigned U.S. Pat. No. 5,336,741 discloses amorphous, partially fluorinated polymers containing selected cyclic units.

D. J. Burton, et al., J. Fluorine Chem., vol. 50, p. 257–264 (1990) describe the synthesis of 1,1,2,3,3-pentafluoro-1,5-heaxdiene. No homologs are described.

SUMMARY OF THE INVENTION

This patent concerns a polymer, comprising, one or more of the repeat units

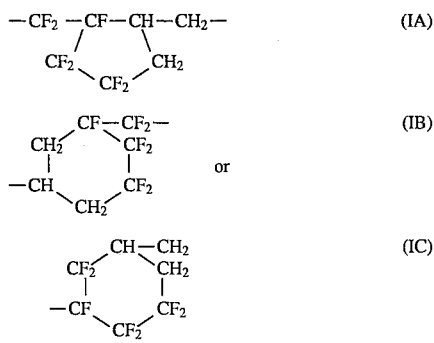

or one or more of the repeat units

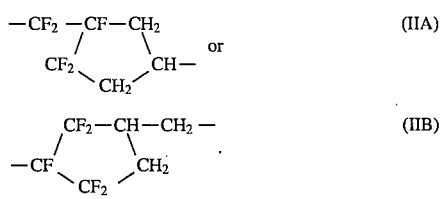

This invention also concerns a compound of the formula $CF_2=CFCF_2CF_2CH_2CH=CH_2$.

Further disclosed herein is a free radical polymerization process, comprising, contacting, in the liquid phase, $CF_2=CFCF_2CH_2CH=CH_2$ with a free radical initiator, under conditions in which said free radical initiator generates free radicals.

DETAILS OF THE INVENTION

The compounds $CF_2=CF(CF_2)_nCH_2CH=CH_2$, wherein n is 1 or 2, can be free radically polymerized to polymers containing one or more cyclic structures. When n is 2, a polymer with one or more of the repeat units (IA), (IB), and (IC) is produced. When n is 1, a polymer with one or more of the repeat units (IIA) and (IIB) is produced. The synthesis of these two monomers is described in Examples 1 and 2 and Experiments 1 and 2.

These monomers may be polymerized by themselves to form homopolymers, or copolymerized with other monomers to form copolymers. By "comprising" in describing these polymers is meant that they contain the above cyclic repeat units, plus any other repeat units from other monomers. Suitable comonomers include fluorinated and unfluorinated compounds such as tetrafluoroethylene, hexafluoropropylene, vinylidene fluoride, perfluoro(alkyl vinyl ether), methyl vinyl ether, propylene, ethylene, chlorotrifluoroethylene, and perfluoro(2,2-dimethyl-1,3-dioxole). Preferred comonomers are tetrafluoroethylene, perfluoro(propyl vinyl ether) and perfluoro(2,2-dimethyl-1,3 -dioxole), and tetrafluoroethylene is especially preferred.

The homo- and copolymers described herein are useful for films, coatings, and for molded articles. Such items can be made by standard techniques. Since these polymers are at least partially fluorinated, they have superior chemical resistance, and in many cases superior thermal properties.

The polymerizations described herein may be done by methods well known to the artisan, see for instance polymerizations methods described in H. Mark, et al., Ed., Encyclopedia of Polymer Science and Engineering, vol. 16, John Wiley & Sons, New York, 1989, p. 577–648. The polymerizations may be done neat, in aqueous emulsion or suspension, in solution or organic suspension. They may be done in batch, semibatch or continuous operations. A free radical polymerization initiator is used, suitable initiators including peroxides such as perfluoro(propionyl peroxide) (3P), azonitriles such as azobis(isobutylronitrile) (AIBN), and redox initiators such as persulfate-bisulfite. As is well known, the process is run at a temperature at which the initiator generates free radicals. Process temperatures are generally in the range of about –30 degrees C. to about 200 degrees C., depending upon the initiator selected.

Although the polymerizations are run in a conventional manner, the results of the free radical polymerization of $CF_2=CFCF_2CH_2CH=CH_2$ (III) gave surprising and very unusual results. FIGS. 1 and 2 show the Differential Scanning Calorimetry (DSC) traces for two different homopolymers of (III). The polymer of FIG. 1 was made using AIBN as the initiator, as described in Example 9. The polymer of FIG. 2 was made using 3P as the initiator, as described in Example 10. These two traces show that even though a "homopolymer" is made (there is only one monomer present), two different polymers are produced. This is very unusual.

It is hypothesized this result is due to differing relative amounts of (IIA) and (IIB) in these two homopolymers, and that this difference is due to the differing initiators used. One of the initiators, 3P, is relatively (to AIBN) electron deficient, and it is hypothesized this is the cause of the differing polymers produced.

In the Examples, the following abbreviations are used:
AIBN—azobis(isobutyronitrile)
DSC—differential scanning calorimetry
DMF—N,N-dimethylformamide
FC-75—perfluorotetrahydrofuran
PDD—perfluoro (2,2-dimethyl-1,3-dioxole)
PTFE—polytetrafluoroethylene
TGA—thermogravimetric analysis Glass transition temperatures were taken as the beginning of the transition, while melting points were taken as the peak of the melting endotherm. The heating rate for the DSC was 20° C./min.

EXAMPLE 1

Preparation of $CF_2ClCFClCF_2CF_2CH_2CHICH_2OAc$

To a stirred solution of 20 g of allyl acetate, 10 mL of hexane and 2.0 g of $Pd(PPh_3)_4$ was added 56.8 g of $CF_2ClCFClCF_2CF_2I$ at room temperature. Exothermic reaction occurred and the mixture was stirred overnight and then distilled to give 53.5 g of $CF_2ClCFClCF_2CF_2CH_2CHICH_2$ OAc, bp 89°–90° C./0.3 mm Hg. $^{19}$F NMR: −64.0 (m, 2F), −110 to −112.8 (m, 2F), −116.1 (m, 2F), −130.8 (m, 1F). $^1$H NMR: 4.44–4.28 (m, 3H), 3.05–2.70 (m, 2H), 2.13 (s, 3H). Anal: Calcd for $C_9H_8F_7Cl_2IO_2$: C, 22.57; H, 1.68; F, 27.77; Cl, 14.80; I, 26.50. Found: C, 23.01; H, 1.85; F, 28.92; Cl, 14.79; I, 26.08.

EXAMPLE 2

Preparation of $CF_2=CFCF_2CF_2CH_2CH=CH_2$

To a stirred solution of 10.5 g of Zn and 20 mL of DMF was slowly added 0.5 g of $BrCH_2CH_2Br$ at 80° C. After the mixture was stirred for 10 min, 24 g of $CF_2ClCFClCF_2CF_2CH_2CHICH_2OAc$ was slowly added and the resulting mixture was stirred for 2 hours. Volatiles (6.8 g) were transferred to a −78° C. trap at 13 kPa (absolute) and then redistilled to give 6.2 g of pure $CF_2=CFCF_2CF_2CH_2CH=CH_2$, bp 87° C. $^{19}$F NMR: −90.7 (ddt, J=55.3 Hz, J=38.1 Hz, J=5.7 Hz, 1F), −107.4 (ddtt, J=112.7 Hz, J=55.3 Hz, J=26.9 Hz, J=3.4 Hz, 1F), −115.2 (tm, J=18.5 Hz, 2F), −119.6 (ddd, J=26.9 Hz, J=14.5 Hz, J=5.7 Hz, 2F), −188.3 (ddt, J=112.7 Hz, J=38.1 Hz, J=14.5 Hz, 1F). $^1$H NMR: 5.75–5.90 (m, 1H), 5.70 (m, 2H), 2.82 (m, 2H). IR: 1789 (s), 1653 (m), 1368 (s), 1318 (s), 1272 (s), 1108 (s). Anal: Calcd for $C_7H_5F_7$: C, 37.85; H, 2.27. Found: C, 37.62; H, 2.28.

EXPERIMENT 1

Preparation of $CF_2=CFCF_2CH_2CHICH_2OAc$

A mixture of 27.0 g of perfluoroallyl iodide, 18 g of allyl acetate and 1.4 g of copper powder was stirred at 48° C. under $N_2$ overnight. The condenser was replaced with a distillation head and the mixture was distilled in vacuum to give 31.5 g of $CF_2=CFCF_2CH_2CHICH_2OAc$, bp 92° C./665 Pa. $^{19}$F NMR: −93.6 (ddt, J=60.2 Hz, J=35.8 Hz, J=5.1 Hz, 1F), −99.0 (dm, J=280 Hz, 1F), −103.4 (dm, J=280 Hz, 1F), 108.0 (ddt, J=144.9 Hz, J=58 Hz, J=28.2 Hz, 1F). $^1$H NMR: 4.35–4.20 (m, 3H), 2.88–2.72 (m, 2H), 2.08 (s, 3H). IR: 2958 (w), 1788 (s), 1749 (s), 1316 (s), 1290 (s), 1172 (s), 1125 (s), 995 (s). Anal: Calcd for $C_8H_8F_5IO_2$: C, 26.84; H, 2.25; F, 26.53. Found: C, 26.91; H, 2.27; F, 25.28.

EXPERIMENT 2

Preparation of $CF_2=CFCF_2CH_2CH=CH_2$

To a stirred solution of 6.5 g of Zn and 20 mL of DMF was added 0.5 g of 1,2-dibromoethylene at 80° C. After the resulting mixture was stirred for 20 min, 25.0 g of $CF_2=CFCF_2CH_2CHICH_2OAc$ (Experiment 1) was slowly added over 35 min at 80° C. After the addition was complete, the reaction mixture was stirred for 30 min. Volatile materials (9.6 g, 99.8% pure) were collected in a dry ice-acetone trap under partial vacuum (26.6 kPa). Redistillation gave 9.1 g of $CF_2=CFCF_2CH_2CH=CH_2$, bp 63°–64° C. $^{19}$F NMR: −95.9 (ddt, J=64.9 Hz, j=36.2 Hz, J=5.3 Hz, 1F), −101.7 (m, 2F), −109.7 (ddt, J = 114.5 Hz, J=64.5 Hz, J=27.2 Hz, 1F), −188.9 (ddt, J= 115 Hz, J=36.2 Hz, J=13.7 Hz, 1F). $^1$H NMR: 5.82–5.69 (m, 2H), 5.32–5.27 (m, 1H), 2.86 (td, J=15.8 Hz, J=7.1 Hz, 2H).

EXAMPLE 3

Homopolymerization of $CF_2=CFCF_2CH_2CH=CH_2$ initiated by bis(perfluoropropionyl) peroxide A 25 mL glass ampul fitted with a PTFE coated stir bar was charged with 0.3 mL of 5% of bis(perfluoropropionyl) peroxide in 1,1,2-trichlorotrifluoroethane and 0.8 g of the title compound. The ampul was sealed and cooled in a liquid nitrogen bath. After being evacuated and purged with $N_2$ alternately six times, contents of the sealed ampul were stirred at 40° C. for 23 hours. The white heterogenous mixture was filtered, washed with ethyl acetate, and dried under vacuum at 100° C. to give 0.36 g of polymer.

The IR spectrum of this polymer showed no absorption at around 1790 and 1650 cm$^{-1}$ which could be attributed to double bonds in the polymer.

This polymer was insoluble in acetone, ethyl acetate, tetrahydrofuran and DMf, hexafluorobenzene and FC-75. The polymer had a glass transition temperature of 113° C., a crystallization temperature of 177° C. and a melting point of 260° C. by DSC (second heat). By TGA the polymer showed 10% weight loss at temperatures of about 445° C. in nitrogen and 410° C. in air, respectively, when heated at 20° C./minute.

EXAMPLE 4

Homopolymerization of $CF_2=CFCF_2CH_2CH=CH_2$ initiated by bis(perfluoropropionyl) peroxide in CFC-113

A 75 mL glass ampul fitted with a PTFE coated stir bar was charged with 0.8 mL of 5% of bis(perfluoropropionyl) peroxide in 1,1,2-trichlorotrifluoroethane (CFC113), 6.0 g of the title compound and 25 g of 1,1,2-trichlorotrifluoroethane. The ampul was sealed and cooled in a liquid nitrogen bath. After being evacuated and purged with $N_2$ alternately six times, contents of the sealed ampul were stirred at 40° C. for 22 hours. The white heterogenous mixture was filtered and washed with CFC113 and dried under vacuum at 100° C. to give 0.25 g of polymer. Anal: Calcad for $C_7H_5F_7$: C, 37.85; H, 2.27. Found: C, 36.82; H, 2.17.

This polymer was insoluble in acetone, ethyl acetate, tetrahydrofuran and DMF, hexafluorobenzene and FC-75. The polymer had a glass transition temperature of 106° C. and a melting point of 258° C. by DSC (second heat), and no crystallization temperature was observed. By TGA the polymer showed 10% weight loss at temperatures of about 445° C. in nitrogen and 420° C. in air, respectively, when heated at 20° C./minute.

EXAMPLE 5

Homopolymerization of
$CF_2=CFCF_2CF_2CH_2CH=CH_2$ initiated by AIBN in CFC113

A 50 mL glass ampul fitted with a PTFE coated stir bar was charged with 90 mg of AIBN, 6.0 g of the title compound and 10 mL of in 1,1,2-trichlorotrifluoroethane (CFC113). The ampul was sealed and cooled in a liquid nitrogen bath. After being evacuated and purged with $N_2$ alternately six times, contents of the sealed ampul were stirred at 70° C. for 60 hours. The white heterogenous solution were filtered and washed with CFC113 and dried under vacuum at 110° C. to give 3.5 g of polymer.

This polymer was insoluble in acetone, ethyl acetate, tetrahydrofuran and DMF, hexafluorobenzene and FC-75. The polymer had a glass transition temperature of 108° C. and a melting point of 260° C. by DSC (second heat), and no crystallization temperature was observed. By TGA the polymer showed 10% weight loss at temperatures of about 445° C. in nitrogen and 420° C. in air, respectively, when heated at 20° C./minute.

EXAMPLE 6

Copolymerization of
$CF_2=CFCF_2CF_2CH_2CH=CH_2$ with
perfluoropropyl vinyl ether (PPVE)

A 25 mL glass ampul fitted with a PTFE coated stir bar was charged with 20 mg of AIBN, 2 mL of 1,1,2-trichlorotrifluoroethane, 1.0 g of $CF_2=CFCF_2CF_2CH_2CH=CH_2$ and 1.0 g of PPVE. The ampul was sealed and cooled in a liquid nitrogen bath. After being evacuated and purged with $N_2$ gas six times, contents of the sealed ampul were stirred at 65° C. for 20 hours and 70° C. for 48 hours. After removal of CFC113, white solids were dissolved in ethyl acetate, reprecipitated by addition of methanol containing 20% water and dried under vacuum at 100° C. to give 0.38 g of polymer. The polymer had a glass transition temperature of 106° C. and a melting point of 253° C. by DSC (second heat). By TGA the polymer showed 10% weight loss at temperatures of about 440° C. in nitrogen and 420° C. in air, respectively, when heated at 20° C./minute.

EXAMPLE 7

Copolymerization of $CF_2=CFCF_2CF_2CH_2CH=CH_2$ with PDD

A 25 mL glass ampul fitted with a PTFE coated stir bar was charged with 0.35 mL of 5% of bis (perfluoropropionyl) peroxide in 1,1,2-trichlorotrifluoroethane and 0.6 g of $CF_2=CFCF_2CF_2CH_2CH=CH_2$ and 0.6 g of PDD. The ampul was sealed and cooled in a liquid nitrogen bath. After being evacuated and purged with $N_2$ alternately six times, contents of the sealed ampul were stirred at 40° C. for 23 hours. The white heterogenous solution were filtered and washed with ethyl acetate and dried under vacuum at 100° C. to give 0.63 g of polymer. The polymer had a glass transition temperature of 109° C. and a metaling point of 262° C. by DSC (second heat). By TGA the polymer showed 10% weight loss at temperatures of about 445° C. in nitrogen and 410° C. in air, respectively, when heated at 20° C./minute.

EXAMPLE 8

Copolymerization of
$CF_2=CFCF_2CF_2CH_2CH=CH_2$ with
Tetrafluoroethylene

A 100 mL shaker tube was charged with 10 mL of 1,1,2-trichlorotrifluoroethane, 2.5 mL of 5% of bis(perfluoropropionyl) peroxide in CFC113, 6.0 g of $CF_2=CFCF_2CF_2CH_2CH=CH_2$. After being sealed, the tube was cooled, evacuated and pressured with 6 g of tetrafluoroethylene. The contents were shakered at 40° C. for 15 hours and 60° C. for 2 hours. The suspension was filtered and the solids were washed with CFC113 for four times and dried in vacuum at 80° C. to give 4.5 g of polymer. The polymer had a glass transition temperature of 104° C. and no melting point by DSC (second heat). By TGA the polymer showed 10% weight loss at temperatures of about 410° C. in nitrogen and 390° C. in air, respectively, when heated at 20° C./minute.

It could be obtained as a colorless and transparent thin film upon removing solvent from its solution in hexafluorobenzene spread on a glass plate.

EXAMPLE 9

Homopolymerization of
$CF_2=CFCF_2CH_2CH=CH_2$ initiated by AIBN

A 25 mL glass ampul fitted with a PTFE coated stir bar was charged with 20 mg of AIBN and 1.12 g of the title compound. The ampul was sealed and cooled in a liquid nitrogen bath. After being evacuated and purged with $N_2$ alternately six times, contents of the sealed ampul were stirred at 65° C. for 60 hours. The white heterogenous mixture was filtered and washed with CFC113 and dried under vacuum at 100° C. to give 0.13 g of polymer.

The polymer had a glass transition temperature of 110° to 184° C. and no melting point by DSC (second heat). By TGA the polymer showed 10% weight loss at temperatures of about 440° C. in nitrogen and 415° C., in air respectively, when heated at 20° C./minute.

EXAMPLE 10

Homopolymerization of
$CF_2=CFCF_2CH_2CH=CH_2$ initiated by
bis(perfluoropropionyl) peroxide A 25 mL glass ampul fitted with a PTFE coated stir bar was charged with 0.3 mL of 5% of bis(perfluoropropionyl) peroxide in 1,1,2-trichlorotrifluoroethane and 1.0 g of the title compound. The ampul was sealed and cooled in a liquid nitrogen bath. After being evacuated and purged with $N_2$ alternately six times, contents of the sealed ampul were stirred at 40° C. for 60 hours. The white beterogenous mixture was filtered and washed with CFC113 and dried under vacuum at 100° C. to give 0.10 g of polymer.

The polymer had no glass transition by DSC and temperatures by TGA the polymer showed 10% weight loss at temperatures of about 450° C. in nitrogen and 415° C., in air respectively, when heated at 20° C./minute.

What is claimed is:
1. A compound of the formula $CF_2=CFCF_2CF_2CH_2CH=CH_2$.

* * * * *